US00RE41045E

(19) United States
(12) Reissued Patent
Sluijter et al.

(10) Patent Number: US RE41,045 E
(45) Date of Reissued Patent: *Dec. 15, 2009

(54) METHOD AND APPARATUS FOR ALTERING NEURAL TISSUE FUNCTION

(75) Inventors: Menno E. Sluijter, Amsterdam (NL); William J. Rittman, III, Lynnfield, MA (US); Eric R. Cosman, Belmont, MA (US)

(73) Assignee: Covidien AG, Neuhausen am Rheinfall (CH)

( * ) Notice: This patent is subject to a terminal disclaimer.

(21) Appl. No.: 10/460,506

(22) Filed: Jun. 12, 2003

Related U.S. Patent Documents

Reissue of:
(64) Patent No.: 6,259,952
Issued: Jul. 10, 2001
Appl. No.: 09/410,609
Filed: Oct. 1, 1999

U.S. Applications:
(63) Continuation of application No. 08/671,927, filed on Jun. 27, 1996, now Pat. No. 5,983,141.

(51) Int. Cl.
*A61F 2/00* (2006.01)

(52) U.S. Cl. ..... 607/100; 606/32; 607/116
(58) Field of Classification Search ..... 607/99–102, 607/113–116; 606/32–34, 38–41, 372–374, 606/377, 378
See application file for complete search history.

(56) References Cited

U.S. PATENT DOCUMENTS

| | | | |
|---|---|---|---|
| 919,139 | A | 4/1909 | Duke |
| 3,127,895 | A | 4/1964 | Kendall et al. |
| 3,791,373 | A | 2/1974 | Winkler et al. |

(Continued)

FOREIGN PATENT DOCUMENTS

| | | |
|---|---|---|
| DE | 3151180 | 8/1982 |
| EP | 000811395 | 12/1997 |
| WO | WO8501212 | 3/1985 |
| WO | WO9400188 | 1/1994 |
| WO | WO9713550 | 4/1997 |
| WO | WO974953 | 12/1997 |
| WO | WO984888 | 11/1998 |

OTHER PUBLICATIONS

Cosman & Cosman, "Methods of Making Nervous System Lesions," Neurosurgery, pp. 2490–2499.

Cosman et al., "Theoretical Aspects of Radiofrequency Lesions in the Dorsal Root Entry Zone," Neurosurgery, vol. 15, No. 6, pp. 945–950, 1984.

Guttman et al., "Squid Axion Membrane Response to White Noise Stimulation," Biophysical Journal, vol. 14, pp. 941–955, 1974.

Radionics, "RFG–3C Graphics: RF Lesion Generator System with Graphics," 1996.

Salkoff & Kelly, "Atmospheric Electricity and Sun–Weather Relationships," Nature, vol. 273, No. 5658, pp. 3–5, May 11, 1978.

Terman, Frederick Emmons, "Radio Engineering," New York, Mcgraw–Hill Book Company, Inc., 1947.

International Search Report: PCT/US 97/11145, Oct. 13, 1997.

*Primary Examiner*—Michael Peffley

(57) ABSTRACT

A method and apparatus for altering a function of neural tissue in a patient. An electromagnetic signal is applied to the neural tissue through an electrode. The electromagnetic signal has a frequency component above the physiological stimulation frequency range and an intensity sufficient to product an alteration of the neural tissue, the alteration causing the patient to experience a reduction in pain, and a waveform that prevents lethal temperature elecation of the neural tissue during application of the electromagnetic signal to the neural tissue.

40 Claims, 2 Drawing Sheets

U.S. PATENT DOCUMENTS 3,817,254 A 6/1974 Maurer
3,888,261 A 6/1975 Maurer
3,894,532 A 7/1975 Morey
3,897,789 A 8/1975 Blanchard
3,911,930 A 10/1975 Hagfors et al.
3,946,745 A 3/1976 Hsiang-Lai et al.
4,014,347 A 3/1977 Halleck et al.
4,055,190 A 10/1977 Tany
4,177,819 A 12/1979 Kofsky et al.
4,210,151 A 7/1980 Keller, Jr.
4,237,899 A 12/1980 Hagfors et al.
4,324,253 A 4/1982 Greene et al.
4,338,945 A 7/1982 Kosugi et al.
4,340,630 A 7/1982 Doty
4,431,002 A 2/1984 Maurer et al.
4,442,839 A 4/1984 Maurer et al.
4,453,548 A 6/1984 Maurer et al.
4,520,825 A 6/1985 Thompson et al.
4,535,777 A 8/1985 Castel
4,541,432 A 9/1985 Molina-Negro et al.
4,556,064 A 12/1985 Pomeranz et al.
4,565,200 A 1/1986 Cosman
4,640,286 A 2/1987 Thomson
4,671,286 A 6/1987 Renault
4,723,552 A 2/1988 Kenyon et al.
4,735,204 A 4/1988 Sussman et al.
4,759,368 A 7/1988 Spanton et al.
4,790,319 A 12/1988 Slovak
4,793,353 A 12/1988 Borkan
4,887,603 A 12/1989 Morawetz et al.
4,907,589 A * 3/1990 Cosman ..... 606/34
4,917,092 A 4/1990 Todd et al.
4,922,908 A 5/1990 Morawetz et al.
4,929,865 A 5/1990 Blum
4,938,223 A 7/1990 Charters et al.
RE33,420 E 11/1990 Sussman et al.
4,977,895 A 12/1990 Tannenbaum
4,989,605 A 2/1991 Rossen
5,036,850 A 8/1991 Owens
5,052,391 A 10/1991 Silberstone et al.
5,058,605 A 10/1991 Slovak
5,063,929 A 11/1991 Bartelt et al.
5,109,847 A 5/1992 Liss et al.
5,117,826 A 6/1992 Bartelt et al.
5,233,515 A 8/1993 Cosman
5,330,515 A 7/1994 Rutecki et al.
5,342,409 A 8/1994 Mullett
5,350,414 A 9/1994 Kolen
5,370,672 A 12/1994 Fowler et al.
5,417,719 A 5/1995 Hull et al.
5,433,739 A * 7/1995 Sluijter et al. ..... 607/99
5,478,303 A 12/1995 Foley-Nolan et al.
5,562,717 A 10/1996 Tippey et al.
5,569,242 A 10/1996 Lax et al.
5,571,147 A 11/1996 Sluijter et al.
5,573,552 A 11/1996 Hansjurgens
5,584,863 A * 12/1996 Rauch et al. ..... 607/2
5,643,330 A 7/1997 Holsheimer et al.
5,658,322 A 8/1997 Fleming
5,690,692 A 11/1997 Fleming
5,702,428 A 12/1997 Tippey et al.
5,702,429 A 12/1997 King
5,759,158 A * 6/1998 Swanson ..... 600/508
5,800,481 A 9/1998 Loos
5,814,092 A 9/1998 King
5,817,139 A 10/1998 Kasano
RE35,987 E 12/1998 Harris et al.
5,908,444 A 6/1999 Azure
5,913,882 A 6/1999 King
5,925,070 A 7/1999 King et al.
5,938,690 A 8/1999 Law et al.
5,948,007 A 9/1999 Starkebaum et al.
5,951,546 A 9/1999 Lorentzen
5,983,141 A 11/1999 Sluijter et al.
6,035,236 A 3/2000 Jarding et al.
6,161,044 A 12/2000 Silverstone
6,275,735 B1 8/2001 Jarding et al.

* cited by examiner

METHOD AND APPARATUS FOR ALTERING NEURAL TISSUE FUNCTION

Matter enclosed in heavy brackets [ ] appears in the original patent but forms no part of this reissue specification; matter printed in italics indicates the additions made by reissue.

RELATED APPLICATION

This application is a continuation of application Ser. No. 08/671,927 filed on Jun. 27, 1996, now U.S. Pat. No. 5,983,141.

BACKGROUND OF THE INVENTION

The use of radiofrequency (rf) generators and electrodes to be applied near or in neural tissue for pain relief or functional modification is well known. For instance, the RFG3C RF Lesion Generator of Radionics, Inc., Burlington, Mass., and its associated electrodes enable placement of the electrode near neural tissue and heating of that tissue by rf resistive power dissipation of the generator power in the tissue. Thermal monitoring by thermo sensor in the electrode has been used to control the process. Heat lesions with tissue temperatures of 60 to 95 degrees Celsius (° C.) are common. tissue dies by heating at about 45 to 50° C., so this process is a heat lesion generation and is designed to elevate the neural tissue above this lethal temperature threshold. Often, the procedure of heating above 45 to 50° C. causes severe pain to the patient which is so unpleasant and frequently unbearable that local or general anesthetic is required during the heat procedure. Use of such anesthetics has a degree of undesired risk to the patient, and the destructive nature of and unpleasant side effects of the rf heat lesion are limitations of this technique, which is well known. Heat lesion generators typically use continuous wave rf generators with radiofrequencies of between 100 KiloHertz to several MegaHertz (viz. the rf generators of Radionics, Fischer, OWL, Elekta, Medtronic, Osypka, EPT companies). The theory and use of rf lesion generators and electrodes for pain and functional disorders is described in various papers; specifically see: (1) Cosman, et al. "Theoretical Aspects of Radiofrequency Lesions and the Dorsal Root Entry Zone." Neurosurg 15:945–950, 1984; and (2) Cosman E R and Cosman B J. "Methods of Making Nervous System Lesions," in Wilkins R H, Rengachary S S (eds): Neurosurgery. New York, McGraw-Hill, Vol. III, 2490–2498, 1984.

Neural stimulation is also now a common method of pain therapy. Stimulus generators with outputs of 0 to 10 volts (or zero to several milliamperes of current criteria are used) are typical. A variety of waveforms and pulse trains in the "physiologic" frequency ranges of 0 to about 300 Hertz are also typical. This output is delivered to electrodes placed near or in neural tissue on a temporary basis (acute electrode placement) or permanent basis (chronic electrode implants). Such stimulation can relieve pain, modify neural function, and treat movement disorders. Typically, the stimulation is sustained to have a long-term effect, i.e. usually when the stimulus is turned off, the pain will return or the therapeutic neural modification will cease after a short time (hours or days). Thus permanent implant electrodes and stimulators (battery or induction driven) is standard practice (viz. see the commercial systems by Medtronic, Inc., Minneapolis, Minn.), and the stimulus is usually sustained or repeated on an essentially continuous basis for years to suppress pain or to treat movement disorders (viz. Parkinsonism, bladder control, spasticity, etc.). Stimulators deliver regular pulse trains or repetitive bursts of pulses in the range of 0 to 200 Hertz (i.e., a physiologic range similar to the body's neural frequency pulse rates), so this method simulates or inhibits neural function at relatively low frequency. It does not seek to heat the neural tissue for destructive purposes as in high frequency technique. Chronically or permanently implanted stimulators often require battery changes or long-term maintenance and patient follow-up, which is expensive and inconvenient, often requiring repeated surgery.

Electrosurgical generators have been in common use for decades cutting and coagulating tissue in surgery. They typically have a high frequency, high power generator connected to an electrode that delivers a high power output to explode tissue for tissue cutting and to cook, sear, and coagulate tissue to stop bleeding. Examples are the generators of Codman, Inc., Randolph Mass., Valley Labs, Inc., Boulder, Colo., and EMC Industries, Montrouge, France. Such generators have high frequency output waveforms which are either continuous waves or interrupted or modulated waves with power controls and duty cycles at high levels so that tissue at the electrode is shattered and macroscopically separated (in cutting mode) or heated to very high temperatures, often above cell boiling (100° C.) and charring levels (in coagulation or cauterizing mode). The purpose of electrosurgery generators is surgical, not therapeutic, and accordingly their output controls, power range, duty cycle, waveforms, and monitoring is not designed for gentle, therapeutic, neuro-modulating, sub-lethal temperature application. Use of an electrosurgical unit requires local or general anesthetic because of its violent and high-temperature effect on tissues.

SUMMARY OF THE INVENTION

The present invention is directed to a modulated high frequency apparatus in conjunction with a signal applicator (for example an electrode or conductive plate or structure applied to the body) to modify neural function, the associated apparatus and method of use being functionally different from and having advantages over the rf heat lesioning systems, or the stimulation systems, and electrosurgical systems of the type described above. Pain relief or neural modification, for instance, can be achieved by the present invention system without average heating of tissue above 45 to 50° C., without stimulating at frequencies in the range of 0 to about 300 Hertz and without burning or cauterizing tissue. Thus as one advantage of the present invention, painful rf lesioning episodes at high lesion temperatures can be avoided and the need for chronic stimulation can be circumvented.

For example, by using an rf waveform output connected to an electrode inserted into the body near or in neural tissue, and by interrupting the rf waveform with bursts of rf power with interposed periods of off-time, a pain relieving effect or other neural modulating effect is accomplished, but the tissue temperature may not on average exceed approximately 45° C. This avoids the painful heat lesions associated with the typical rf lesions which involve tissue temperatures at a region near the electrode of substantially greater than 45° C. The modulated rf system can be used painlessly and easily, avoiding usual discomforts of standard rf heating procedures, yet relief of the pain or the neural disfunction (such as for example motor disfunction, spasticity, Parkinsonism, tremors, modd disorders, incontinence, etc.) can be long lasting using the novel system of the present invention, giving results in many cases that are comparable to those of rf heat lesions done at much higher temperatures. Some applications of this invention may include such examples as relief of back, head, and facial pain by procedures such as dorsal root ganglion or trigeminal ganglion treatments, spinal cord application for relief of intractable pain, spasticity, or motor control, treatment of the basal ganglia in the brain for relief of Parkinsonism, loss of motor control, tremors, or intractible pain. This pain relief or control or elimination of motor or other neural disfunction can be comparable if not more effective than long-term stimulators with implanted electrodes, thus avoiding the need for permanent implants, expensive implanted devices and circuits, battery changes, involving repeated surgery and expense, and repeated application of stimulation energy over long periods (months and years). The pain relief or neural modification can be accomplished by the present invention in a non-violent, painless way, avoiding average tissue temperature elevations into the lethal range and violent macroscope tissue separations, and thus the present invention is opposite to the objectives, systems, and methods involved in electrosurgical systems.

Forms of the modulated frequency generator and output waveforms are disclosed herein in various embodiments. Specific embodiments with temperature monitors and thermal sensing electrodes are disclosed which are suited to control the modulated system and its use.

BRIEF DESCRIPTION OF THE DRAWINGS

In the drawings, which constitute a part of the specification, exemplary embodiments exhibiting various forms and features hereof are set forth, specifically.

DESCRIPTION OF THE INVENTION

Figure 1:
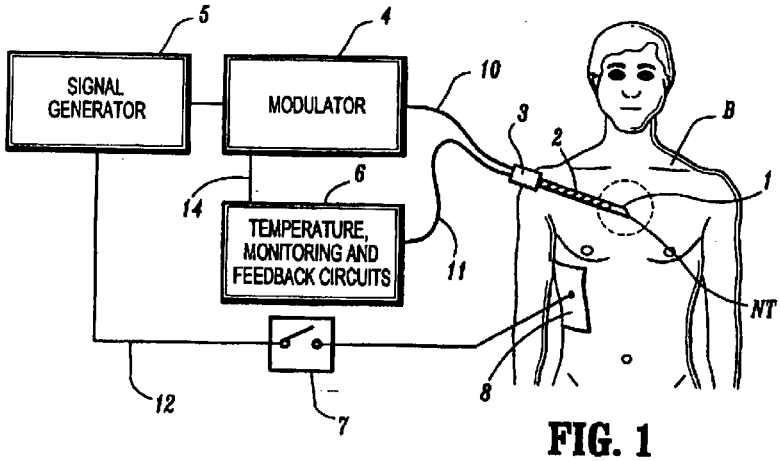
FIG. 1 is a block diagram of elements of a system in accordance with the present invention.

Referring to FIG. 1, an illustration of the present invention is shown in block diagram and schematic elements. An electrode with uninsulated conductive surface 1 (for example a conductive tip end) is in proximity to a region of neural tissue NT (viz. illustrated schematically by the dashed boundary). The electrode has an insulated shaft 2 and connection or hub portion 3, inside of which there can be electric connections to surface 1. Connection 10 electrically connects to the surface 1 through the electrode shaft 2 and to electronic supply units 4 and 5 (which are shown outside the body, but which may be miniaturized and implanted inside the body). Element 5 is a signal generator of signal output (viz., voltage, current, or power), and element 4 is a modulator to modulate (for example the amplitude of) the high frequency output from 4. The electromagnetic output from 4 and 5 is connected to electrode surface 1, and therefore is conductively exposed to tissue NT. As an example, element 5 can take the form of an rf power source with a continuous wave output (viz. for example, similar to the model RFG-3C generator of Radionics, Inc., Burlington, Mass.). Element 4 is a pulse modulation unit which switches on and off the rf output from 5 at a designed rate and duty cycle. RF output generators or supplies and, modulation circuits are known in high frequency technique (viz. Radio Engineering by Frederick E. Terman, McGraw-Hill, New York, 1947, 3rd Edition). Further shown is a temperature monitoring element or circuit 6 which connects by cable 11 to the electrode and to a thermal sensor (viz. thermistor or thermocouple) inside the electrode applicator or conductive tip 1 to measure the temperature of the tissue NT near the tip. (Such thermal sensing circuits and electrodes are illustrated by the Model RFG-3C and associated thermal-sensing, rf electrodes of Radionics, Inc., Burlington, Mass.). Further, reference electrode 8 is shown in electric contact to the patient's body B with connection wire 12 to generator 5 so as to provide a circuit for return current from electrode applicator 1 through the patient B (such reference electrodes are common with rf lesion generators; see Cosman, et al., 1984). Element 7 is a switch or circuit breaker which illustrates that such a return circuit could be opened to limit such direct return current, and limit such current to inductive or reactive current characteristic of time varying circuits such as rf circuits.

In operation, the voltage or current output from generator 4 and modulator 5 are impressed upon tissue NT, which may be neural tissue (viz. spinal nerves or roots, spinal cord, brain, etc.) or tissue near neural tissue. In accordance with the present invention, such electromagnetic output can cause energy deposition, electric field effects, and/or electromagnetic field effects on the nerve cells in the tissue NT so as to modify or destroy the function of such nerve cells. For example, such modification of neural function may include reduction or elimination of pain syndromes (such as spinal facet, mechanical back pain, facial pain) in some cases, alleviating motor disfunction, spasticity, Parkinsonism, etc., epilepsy or mood disorders. Because the rf output from 4 is modulated by element 5, its percent on-time is reduced so that sustained heating of tissue NT is reduced, yet the neural therapeutic effects of the impressed rf voltages and currents on the neural tissue NT are enough to produce the pain reducing result. The generator 5 can have a power, voltage, or current output control 5A (as on the Radionics Model RFG-3C rf generator) to increase or decrease the output power magnitude or modulated duty cycle to prevent excessive heating of tissue NT or to grade the level of pain interruption as needed clinically. Output control 5A may be a knob which can raise or lower the output in a smooth, venerated way, or it can be an automatic power control with feedback circuits. In this regard, temperature monitor 6 can provide the operator with the average temperature of tissue NT near electrode tip 1 to interactively prevent temperatures near tip 1 to exceed the range of approximately 45° C. (on average thermally lethal to tissue NT), and thus to avoid the higher temperature ranges for the usual heat lesioning procedures described above. For example, 6 may have feedback circuitry to change the modulation duty cycle (by, for example, longer or shorter on-times) to hold the temperature near tissue NT to below a set value (viz. 40 to 45° C.), illustrated by the feedback line 14 in FIG. 1. In addition, the high frequency waveform from the generator 5 can be free from substantial components in the 0 to about 300 to 400 Hertz range (which is much lower than radiofrequencies), and this will avoid the stimulation effects that are typical for stimulator system applications as described above.

Figure 2:
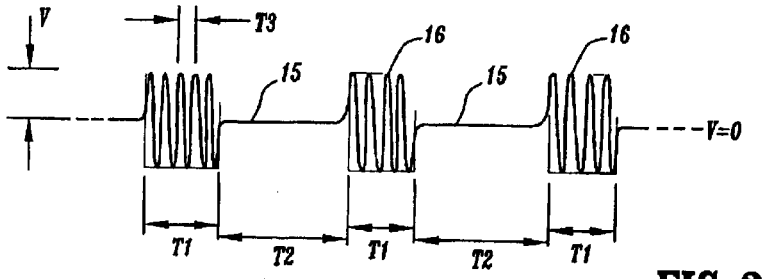
FIG. 2 is a graphical representation of an interrupted rf waveform output from an rf generator system in accordance with the present invention.

As an example of a modulated rf waveform that accommodates the system of the present invention, FIG. 2 shows schematically a high frequency output of voltage amplitude V and of burst duration T1 between which on-time bursts there are illustrated periods of zero voltage of duration T2. During the on-time T1, the rf signal output is oscillatory with time period T3 between maximum voltages V. The reciprocal of T3 is proportional to the value of the radiofrequency (viz., 1 Mega Hertz rf output corresponds to T3=1 microsecond). This is an interrupted or bursting type of modulated high frequency waveform. During the high frequency on-time T1, the voltage can oscillate between plus and minus its maximum value V. Accordingly, an electric field is produced around the region of the electrode applicator (as for instance the exposed electrode tip 1 in FIG. 1). The electric field has a modifying, or pain-relieving, or neural-altering effect on the tissue near or among the nerve cells and fibers. Pain relief and neural modification can accordingly be accomplished by this high frequency bursting voltage and accompanying electromagnetic field, and also accompanying current among the neural and tissue cells. During the off period, there is minimal or no voltage (i.e. V=0 at the electrode applicator), and thus no electric field or electric currents in and among the neural tissue. During that period, no heat deposition is present. Thus, over the entire cycle, from on period T1 through off period T2, the energy deposition, on average, can be adjusted so that there is not excessive heating, on average, around the electrode applicator. Thus, the usual mechanism of continuous on-time high frequency voltage and current, as in previous heat lesion techniques, is avoided, and therefore the achievement of high average temperatures near or around the applicator tip may be eliminated by the present invention. The usual heat lesion process in which tissue temperatures, on average, exceed 45° can be avoided. In many instances, this avoidance of high temperature domains due to high average heat dissipation of the radiofrequency power will prevent acute pain of the process to the patient. By having the interrupted waveform, as in FIG. 2, the average power is thereby reduced and the average heating around the electrode tip or applicator is accordingly reduced. However, substantial voltages V (or currents) can still be sustained during the on period with their resulting therapeutic effect on the tissue.

To give a representative example of values for parameters in an interrupted high frequency waveform as in FIG. 2, the overall pattern of the waveform may have a total period of one second, meaning that the sum of T1+T2=1 second. The on period T1 can be 20 milliseconds, and the off period T2, therefore, can be 980 milliseconds. Voltages V in the range of 10 to 30) volts or more can be used. It can be used with a pain relieving effect in certain tissues. Average tip temperature around an electrode tip such as the exposed tip element 1 in FIG. 1 can be maintained at or below 40° C., well below thermo-lethal levels. Electrodes with diameters of 1 or 2 mm shaft (for example the shaft 2 of a cannula in FIG. 1), with an exposed tip of 1 to 10 mm (such as the tip element 1 in FIG. 1) can be used and the electrode can be inserted in around neural structures in the brain or peripheral nerves or peripheral nerve ganglia to accomplish pain relief or other neurological alteration. Variation of these parameters can be made with similar therapeutic effect, and various geometries of conductive electrode or applicator can be effective. Illustrations of a wide variety of such electrodes are illustrated by the product line of Radionics, Inc., Burlington, Mass. Pointed or sharpened electrodes (such as illustrated schematically by electrode tip 1 in FIG. 1) are useful for penetration of the electrode through the skin to the target neural tissue site, and electric or current fields of higher intensity will be present at a sharpened point for a given applied voltage (such as V in FIG. 2), which will be effective in altering neural function.

Figure 3:
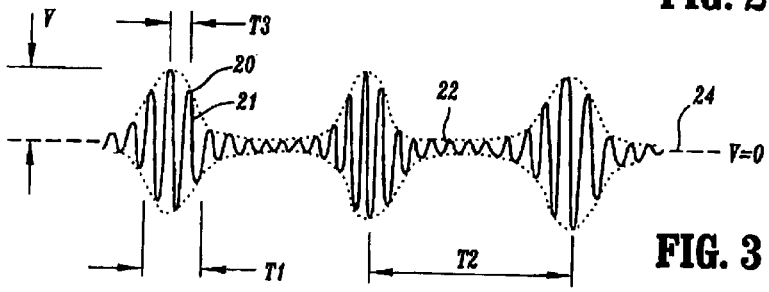
FIG. 3 shows a graph of a modulated frequency waveform of the present invention.

FIG. 3 shows a variation of modulated high frequency waveform which accomplishes high peak voltage swings with reduced average power deposited in tissue. The baseline voltage may be put at zero (viz. V=0), shown by dashed line 24. The solid line 21 represents the actual waveform, which has rapid oscillations at the radiofrequency and has an overall enveloped represented by dashed line 20, that has high points and low points with an approximate on time T1 and a time period between envelope of modulation maxima T2, T1, again, could be a percentage on time of 2 percent (as described above for 20 milliseconds on time out of 1 second total), and this on time T1 may vary considerably while still maintaining substantial off time so as to prevent overall average high temperature heating (as in the usual rf heat lesion systems). Such a modulation envelope (as dashed line 20) can be achieved by using a modulated signal generator that varies the input or output gain of a high frequency generator (as element 5 in FIG. 1) so as to achieve such a waveform is in FIG. 3. In such circuitry, which is commonly used in pulse generation techniques, low frequency filtering or selection of modulation parameters can avoid stimulation voltage or current components at the physiologic range of 0 to 300 Hertz so that unpleasant stimulative effects can be avoided during the therapeutic intermittent high frequency lesion process.

Figure 4:
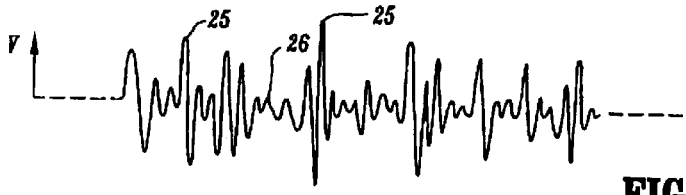
FIG. 4 illustrates an irregular frequency output waveform in accordance with the present invention.

FIG. 4 shows yet another embodiment of an interrupted high frequency waveform in accordance with the present invention. Here there is a non-periodic variation of the voltage represented by the excursions of the voltage V represented by excursions on a vertical axis. The maxima point 25 can occur at random positions in time. The time difference between maxima can also vary in an irregular or even random way. This waveform may have no repeating or periodic structure but may be analogous to high frequency noise with random amplitudes, peaks, zero crossings, and carrier high frequencies. Such a waveform can be generated by random noise generators, spark gap signals, or other noisy signals that are known in the field of signal generation (viz. Radio Engineering, cited above). Filtering can be applied in the wave generator and power amplifier so that lower frequencies in the physiologic range will not be present to give undesirable stimulation effects.

Figure 5:
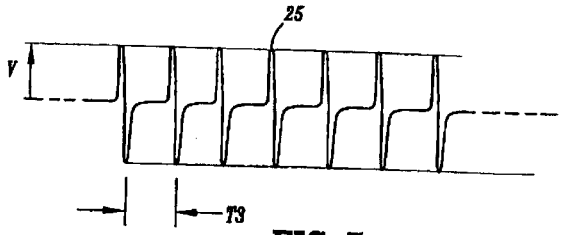
FIG. 5 shows a repeated frequency signal with lowered output duty cycle.

FIG. 5 shows yet another possible high frequency waveform of interrupted, repeated bipolar pulses with frequency repetitive T3 for example the physiologic stimulation frequency range (i.e., 0 to about 300 Hertz). The pulse on-time may be low enough so that the power deposition can be kept low enough to prevent heating, and yet the peak voltage V is enough to alter the neural function.

Variations of such waveforms are possible with the same intermittent high frequency effect for pain on neurological modification. For instance, a baseline V=0 may not pertain and a slowly varying baseline of non-zero value can be used. The time average of the signal need not be zero. The on and off switching of a high frequency signal such as in FIG. 2 can be done at a non-periodic or nonregular, repeating rate so that, on average, the polarization effects in the tissue are still maintained at a low level. The average power deposition can still be maintained at a low level with non-periodic, interrupted high frequency waveforms. The high frequency carrier frequency (i.e. represented by the inverse of time T3 in FIG. 2 and FIG. 3) may also be non-constant. Varying or combined or superposed high frequency waveforms can be used as the carriers, and these combined or composite high frequency waveforms can be interrupted or modulated in accordance with the present system and invention. Pulse waveforms with high frequency carriers can be shaped in a variety of ways, for example with fast rising leading edges and slow or falling off or exponential trailing edges. The signal generator waveform can have a peak intensity which is much higher than the average or RMS intensity to yield a high electromagnetic field or current density on the neural tissue while maintaining the average power deposition in the tissue at a sufficiently low level to prevent heating above lethal tissue temperatures (viz. 40 to 50° C.).

Figure 6:
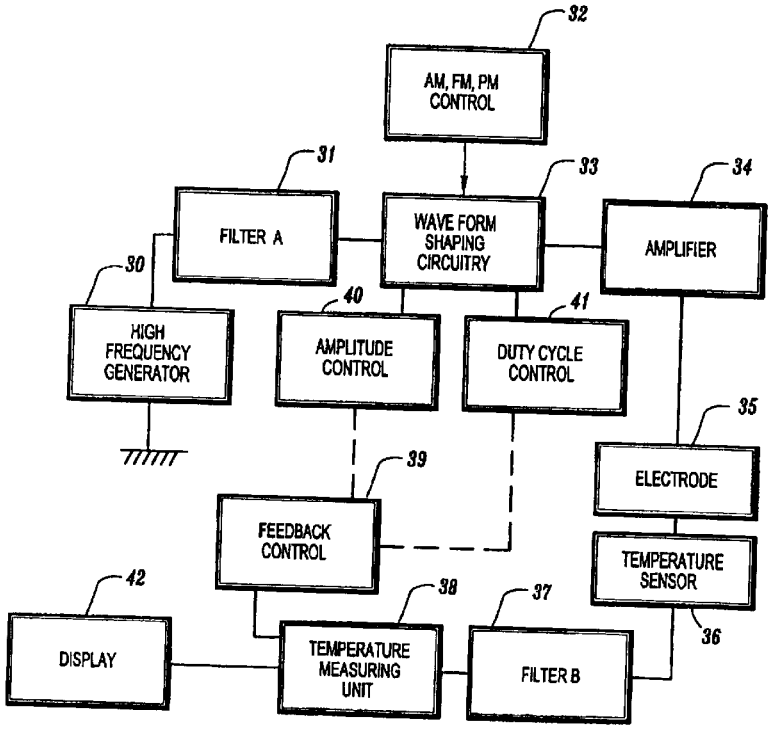
FIG. 6 is a block diagram of elements of a system for generating modulated frequency signals.

FIG. 6 shows a block diagram of a system for generating modulated high frequency signals (similar but in more detail to the block element of high frequency generator 5 and modulator 4 of FIG. 1).

Element 50 represents a signal generator which may create a high frequency signal of periodic or non-periodic frequency. This has input to element 31, which is a filter system which selectively filters out frequencies that could cause unpleasant, undesired, or damaging physiological signals. The signal is then fed into element 33, which is a waveform shaping circuit, and will shape the waveform input from element 32, which provides amplified modulation and/or frequency modulation and/or phase modulation control. Circuits of this type can be found, for instance in Radio Engineering by Terman (cited above). Additional waveform shaping can be done by element 40 and 41, which can control the amplitude of waveform and/or the duty cycle of the waveform, respectively. This resultant signal is then fed into a power amplifier represented of element 34. This is a wide band amplifier used to increase the signal to power levels appropriate for clinical use. This energy is then delivered to the patient via an electrode depicted as element 35.

A temperature sensor or plurality of temperature sensors, represented by element 36, can also be placed and connected in proximity to this electrode so as to insure that the temperature does not exceed desired limits. This temperature sensor signal is fed through element 37, which is a special filter module used to eliminate high frequency components, and thus not to contaminate the low-level temperature signals.

The temperature signal is fed to element 38, which is a standard temperature measuring unit that converts the temperature signal into a signal that can be used to display temperature and/or to control, in a feedback manner, either the amplitude and/or the duty cycle of the high frequency waveform. In this way, power delivery can be regulated to maintain a given set temperature. This flow is represented by element 39, which is simply a feedback control device. The dotted lines from element 39 to elements 40 and 41 represent a feedback connection that could either be electronic and/or mechanical. It could also simply be a person operating these controls manually, based on the visual display of temperature, as for example on a meter or graphic display readout 42.

As was explained with respect to the disclosed embodiments, many variations of circuit design, modulated high frequency waveforms, electrode applicators, electrode cannulas will be appreciated by those skilled in the art for example, electrodes or electrode applicators are practical, including tubular shapes, square shafts, flat electrodes, area electrodes, multiple electrodes, arrays of electrodes, electrodes with side outlets or side-issued tips, electrodes with broad or expandable or conformal tips, electrodes that can be implanted in various portions of the brain, spinal cord, interfecal space, interstitial or ventricular spaces, nerve ganglia can be considered within the system of the present invention.

The frequency range for the so-called high frequency waveforms, as shown for instance in FIGS. 2, 3, 4, and 5 can be used over a wide range. For example, the "high frequency" characteristic of 1/T3, which may be only one of many high frequency components, can be above the so-called physiologic stimulation frequency range of 0 to about 300 Hertz. This high frequency may also range up into the radiofrequency or microwave range (viz. 50 Kilo Hertz to many Mega Hertz).

Mixtures of frequencies can be done as discussed above. These could be admixtures of "high frequencies" (above the physiologic stimulation range (say 0 to 300 Hertz) and lower frequencies (within that stimulation range of say 0 to 300 Hertz). Thus one skilled in the art could have both modulated high frequency and stimulation frequencies for various clinical effects, such as stimulation blockage of pain while neural modification is being applied according to the present invention.

In view of these considerations, as will be appreciated by persons skilled in the art, implementations and systems should be considered broadly and with reference to the claims set forth below.

What is claimed is:

1. A method for sustained neural function modification in a patient comprising:

generating an amplitude modulated signal having at least one frequency component above a physiologic stimulation frequency range; and applying the amplitude modulated signal to selected neural tissue in the patient for altering a function of the tissue without heating the tissue to temperatures lethal to the tissue, *wherein said amplitude modulated signal has a peak voltage, said peak voltage being sufficient to alter the function of the tissue in the patient,* wherein the function remains altered for a given period of time after application of the signal to the tissue is ceased.

2. The method of claim 1 wherein altering the function of the tissue reduces pain experienced by the patient.

3. The method of claim 1 wherein altering the function of the tissue reduces pain by tremor experienced by the patient.

4. The method of claim 1 wherein altering the function of the tissue reduces symptoms of Parkinson's disease experienced by the patient.

5. The method of claim 1 wherein altering the function of the tissue reduces symptoms of spasticity experienced by the patient.

6. The method of claim 1 wherein altering the function of the tissue reduces symptoms of mood disorder experienced by the patient.

7. The method of claim 1 wherein altering the function of the tissue reduces symptoms of epilepsy experienced by the patient.

8. The method of claim 1 wherein altering the function of the tissue alleviates motor disfunction.

9. The method of claim 1 wherein the at least the frequency component of the amplitude modulated signal alters the function of the tissue.

10. The method of claim 1 wherein applying the amplitude modulated signal to the tissue comprises engaging the tissue with an electrode coupled with a signal generator generating the amplitude modulated signal.

11. The method of claim 1 wherein temperatures lethal to the tissue are greater than 45° C.

12. The method of claim 1 wherein the at least one frequency component has a frequency greater than 300 Hz.

13. An apparatus for sustained alteration of a function of selected neural tissue in a patient comprising a signal generator and an electrode coupled to the signal generator, said signal generator being adapted to generate an amplitude modulated signal having at least one frequency component above a physiologic stimulation frequency range, said electrode being adapted to apply the signal to the tissue, wherein application of the amplitude modulated signal to the tissue alters a function of the tissue while inhibiting heating of the tissue to temperatures lethal to the tissue, *wherein said amplitude modulated signal has a peak voltage, said peak voltage being sufficient to alter the function of the tissue in the patient,* and wherein alteration of the function of the tissue persists even after application of the signal to the tissue ceases.

14. The apparatus of claim 13 wherein altering the function of the tissue reduces pain experienced by the patient.

15. The apparatus of claim 13 wherein altering the function of the tissue causes the patient to experience a reduction in pain by tremor.

16. The apparatus of claim 13 wherein altering the function of the tissue causes the patient to experience reduced symptoms of Parkinson's disease.

17. The apparatus of claim 13 wherein altering the function of the tissue causes the patient to experience a reduced symptoms of spasticity.

18. The apparatus of claim 13 wherein altering the function of the tissue causes the patient to experience a reduced symptoms of mood disorder.

19. The apparatus of claim 13 wherein altering the function of the tissue causes the patient to experience a reduced symptoms of epilepsy.

20. The apparatus of claim 13 wherein altering the function of the tissue alleviates motor disfunction.

21. The apparatus of claim 13 wherein the at least one frequency component of the amplitude modulated signal alters the function of the tissue.

22. A method for lasting modification of neural tissue function in a patient comprising:

placing an electrode in or near selected neural tissue of the patient;

generating an amplitude modulated signal and transmitting the signal to the electrode, said signal having at least one frequency component above a physiologic stimulating frequency range for alteration of a function of the tissue without heating the tissue to temperatures lethal to the tissue, *wherein said amplitude modulated signal has a peak voltage being sufficient to alter the function of the tissue in the patient,* said alteration being sustained even after transmission of the signal to the electrode ceases.

23. The method of claim 22 wherein altering the function of the tissue reduces pain experienced by the patient.

24. The method of claim 22 wherein altering the function of the tissue causes the patient to experience a reduction in pain by tremor.

25. The method of claim 22 wherein altering the function of the tissue causes the patient to experience reduced symptoms of Parkinson's disease.

26. The method of claim 22 wherein altering the function of the tissue causes the patient to experience a reduced symptoms of spasticity.

27. The method of claim 22 wherein altering the function of the tissue causes the patient to experience a reduced symptoms of mood disorder.

28. The method of claim 22 wherein altering the function of the tissue causes the patient to experience a reduced symptoms of epilepsy.

29. The method of claim 22 wherein altering the function of the tissue alleviates motor disfunction.

30. The method of claim 22 wherein the at least one frequency component of the amplitude modulated signal alters the function of the tissue.

31. The method of claim 22 wherein temperatures lethal to the tissue are greater than 45° C.

32. The method of claim 22 wherein the at least one frequency component has a frequency greater than 300 Hz.

*33. A method for sustained neural function modification in a patient comprising:*

*generating interrupted radiofrequency waveforms having predetermined time periods of on-time bursts of radiofrequency output of a first predetermined duration followed by relatively substantial off-time periods of very low output at a second predetermined duration; and*

*applying the interrupted radiofrequency waveforms to selected neural tissue in the patient for a predetermined treatment time sufficient to result in alteration of a function of the tissue without heating the tissue to temperatures lethal to the tissue, wherein the interrupted radiofrequency waveforms have a peak voltage sufficient to result in said alteration, wherein the function remains altered for a given period of time after application of the signal to the tissue is ceased.*

*34. The method of claim 33, wherein altering the function of the tissue reduces symptoms experienced by the patient selected from the group consisting of pain, tremor, Parkinson's disease, spasticity, mood disorder, epilepsy, and motor dysfunction.*

*35. The method of claim 33, wherein the step of applying the interrupted radiofrequency waveforms to the tissue includes engaging the tissue with an electrode coupled with a signal generator.*

*36. The method of claim 33, wherein the generating step includes having a ratio of on-time bursts of radiofrequency output to off-time bursts of approximately two percent.*

*37. An apparatus for sustained alteration of a function of selected neural tissue in a patient comprising:*

*a signal generator which generates interrupted radiofrequency waveforms having predetermined time periods of on-time bursts of radiofrequency output of a first predetermined duration followed by relatively substantial off-time periods of very low output at a second predetermined duration,*

*an electrode coupled to the generator and being adapted to apply the interrupted radiofrequency waveforms to the tissue, wherein application of the interrupted radiofrequency waveforms to the tissue alters a function of the tissue while inhibiting heating of the tissue to temperatures lethal to the tissue, wherein the interrupted radiofrequency waveforms have a peak voltage, said peak voltage being sufficient to result in said alteration, and wherein alteration of the function of the tissue persists even after application of the signal to the tissue ceases.*

*38. The apparatus of claim 37, wherein altering the function of the tissue reduces symptoms experienced by the patient selected from the group consisting of pain, tremor, Parkinson's disease, spasticity, mood disorder, epilepsy, and motor dysfunction.*

*39. The apparatus of claim 37, wherein the generator is adapted to apply the interrupted radiofrequency waveforms to the tissue in a ratio of on-time bursts of radiofrequency output to off-time bursts of approximately two percent.*

*40. An apparatus for sustained alteration of a function of selected neural tissue in a patient comprising:*

*a signal generator which generates interrupted radiofrequency waveforms having predetermined time periods of on-time bursts of radiofrequency output of a first*

*predetermined duration followed by relatively substantial off-time periods of very low output at a second predetermined duration;*

*an electrode coupled to the generator and being adapted to apply the interrupted radiofrequency waveforms to the tissue by being surgically inserted in or on the patient, wherein application of the interrupted radiofrequency waveforms to the tissue alters a function of the tissue while inhibiting heating of the tissue to temperatures lethal to the tissue, and wherein alteration of the function of the tissue persists even after application of the signal to the tissue ceases, and wherein the interrupted radiofrequency waveforms have a peak voltage sufficient to alter the neural tissue, and wherein said peak voltage is in a range that includes tens of volts.*

* * * * *